United States Patent
Cheng et al.

(10) Patent No.: US 9,845,473 B1
(45) Date of Patent: Dec. 19, 2017

(54) METHOD FOR IMPROVING IMMUNITY IN SHRIMPS

(71) Applicant: NATIONAL PINGTUNG UNIVERSITY OF SCIENCE & TECHNOLOGY, Pingtung County (TW)

(72) Inventors: Wen-Teng Cheng, Pingtung County (TW); Chin-Chyuan Chang, Pingtung County (TW); Wan-Lin Tsai, Pingtung County (TW)

(73) Assignee: NATIONAL PINGTUNG UNIVERSITY OF SCIENCE & TECHNOLO, Pingtung County (TW)

( * ) Notice: Subject to any disclaimer, the term of this patent is extended or adjusted under 35 U.S.C. 154(b) by 0 days.

(21) Appl. No.: 15/386,572

(22) Filed: Dec. 21, 2016

(30) Foreign Application Priority Data

Nov. 2, 2016 (TW) .............................. 105135598 A (51) Int. Cl.
*C12N 15/113* (2010.01)

(52) U.S. Cl.
CPC ...... *C12N 15/1137* (2013.01); *C12N 2310/14* (2013.01); *C12N 2310/17* (2013.01); *C12N 2320/35* (2013.01)

(58) Field of Classification Search
None
See application file for complete search history.

(56) References Cited

FOREIGN PATENT DOCUMENTS

WO    WO-2006135436 A2 * 12/2006 ........... C12N 15/111

\* cited by examiner

*Primary Examiner* — Tracy Vivlemore
(74) *Attorney, Agent, or Firm* — WPAT, P.C., Intellectual Property Attorneys; Anthony King (57) ABSTRACT

The invention discloses a method for improving immunity in shrimps, by administering a double-stranded RNA specific to tyrosine hydroxylase to a shrimp body to improve immunity of the shrimp body, wherein the double-stranded RNA is administered to the shrimp body by injection into the ventral sinus of the cephalothorax of the shrimp body.

9 Claims, 8 Drawing Sheets

METHOD FOR IMPROVING IMMUNITY IN SHRIMPS

CROSS REFERENCE TO RELATED APPLICATIONS

The application claims the benefit of Taiwan application serial No. 105135598, filed Nov. 2, 2016, the subject matter of which is incorporated herein by reference.

BACKGROUND OF THE INVENTION

1. Field of the Invention

The present invention generally relates to a method for improving immunity in shrimps, and more particularly, to a method for improving immunity in shrimps by a double-stranded RNA specific to tyrosine hydroxylase.

2. Description of the Related Art

Nowadays, shrimp farming is explosion in Taiwan. The farmed shrimps can not only be served as sources of food, but also be exported to foreign countries for economic benefits. In order to reduce the cost, farmed shrimps are usually grown at high densities.

Farming at high densities may result in deterioration of the farming environment; and therefore, the farmed shrimps have a higher mortality due to cross infection. Although addition of antibiotics can reduce the mortality, the abusiveness of antibiotics is the reason that sparks allergic reaction, as well as the cause of drug resistance.

In light of this, it is necessary to provide a method for improving immunity in shrimps.

SUMMARY OF THE INVENTION

It is therefore the objective of this invention to provide a method for improving immunity in shrimps.

One embodiment of the invention discloses a method for improving immunity in shrimps, by administering a double-stranded RNA specific to tyrosine hydroxylase to a shrimp body to improve immunity of the shrimp body.

In a preferred form shown, the double-stranded RNA has a DNA sequences set forth as SEQ ID NOS: 1 and 2, or a DNA sequences set forth as SEQ ID NOS: 3 and 4, or a DNA sequences set forth as SEQ ID NOS: 5 and 6.

In a preferred form shown, the double-stranded RNA is administered to the shrimp body by injection, preferably by injection into the ventral sinus of the cephalothorax.

In a preferred form shown, the shrimp body is 11.63±2.1 g, and the double-stranded RNA is administered to the shrimp body in a dosage of 1-6 µg/g of the shrimp body, preferably in a dosage of 5 µg/g of the shrimp body.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

The shrimp according to the present invention indicates farmed shrimp, including, but not limited to Pacific white shrimp (*Litopenaeus vannamei*), giant tiger prawn (*Penaeus monodon*), Kuruma shrimp (*Marsupenaeus japonicus*), Chinese white shrimp (*Fenneropenaeu schinensis*), Indian prawn (*Fenneropenaeus indicus*), greasyback shrimp (*Metapenaeus ensis barbata*), redtail shrimp (*Penaeus penicillatus*) and giant river prawn (*Macrobrachium rosenbergii*).

The double-stranded RNA specific to tyrosine hydroxylase, TH dsRNA for short, according to the present specification indicates the double-stranded RNA having the nucleic acid sequences corresponding to the sequences of tyrosine hydroxylase, such that by administering the TH dsRNA to a shrimp body, the TH dsRNA is able to block tyrosine hydroxylase activity, which can be appreciated by a person having ordinary skill in the art. For example, the TH dsRNA can have, but not limited to, a DNA sequences set forth as SEQ ID NOS: 1 and 2, a DNA sequences set forth as SEQ ID NOS: 3 and 4, or a DNA sequences set forth as SEQ ID NOS: 5 and 6.

The TH dsRNA can be used to block tyrosine hydroxylase activity; and therefore, the TH dsRNA can be administered to the shrimp body in an effective dosage for improving immunity in shrimps.

As an example, the TH dsRNA can be administered to the shrimp body by injection, preferably by injection into the ventral sinus of the cephalothorax. The ventral sinus near the heart is the centrostigma of haemolymph in shrimps, such that the TH dsRNA can flow towards tissues along haemolymph. In this embodiment, the shrimp body with weight of 11.63±2.1 grams is used, and the effective dosage is 1-6 µg/g, preferably is 5 µg/g.

To evaluate the TH dsRNA shows effect on improving immunity in shrimps, as well as decreasing the mortality caused by attack of pathogens, the following trials are preformed.

Trial (A)

White shrimps, *Litopenaeus vannamei*, are obtained from a commercial farm in Pingtung, Taiwan. The white shrimps are acclimated in the laboratory (freshwater; salinity 20 ppt; temperature 27±1° C.; pH value 8.2-8.7) for 2 weeks before experimentation.

Referring to TABLE 1, the TH dsRNA (SEQ ID NOS: 1 and 2) is administered to white shrimps of group A2 by injection, and the challenge control dsRNAs being not specific to tyrosine hydroxylase are administered to white shrimps of groups A3 and A4 by injection. The dosage for each dsRNA is 5 μg/g. white shrimps of group A1 without dsRNA administration are used as the control. Tyrosine hydroxylase activity is measured 3 days later.

TABLE 1

| Group | double-stranded RNA |
|---|---|
| A1 | DEPC-H$_2$O |
| A2 | dsRNA specific to tyrosine hydroxylase (SEQ ID NOS: 1 and 2) |
| A3 | dsRNA specific to glyceraldehydes 3-phosphate dehydrogenase (SEQ ID NOS: 7 and 8) |
| A4 | dsRNA specific to worm non-specific gene (SEQ ID NOS: 9 and 10) |

Figure 1A:
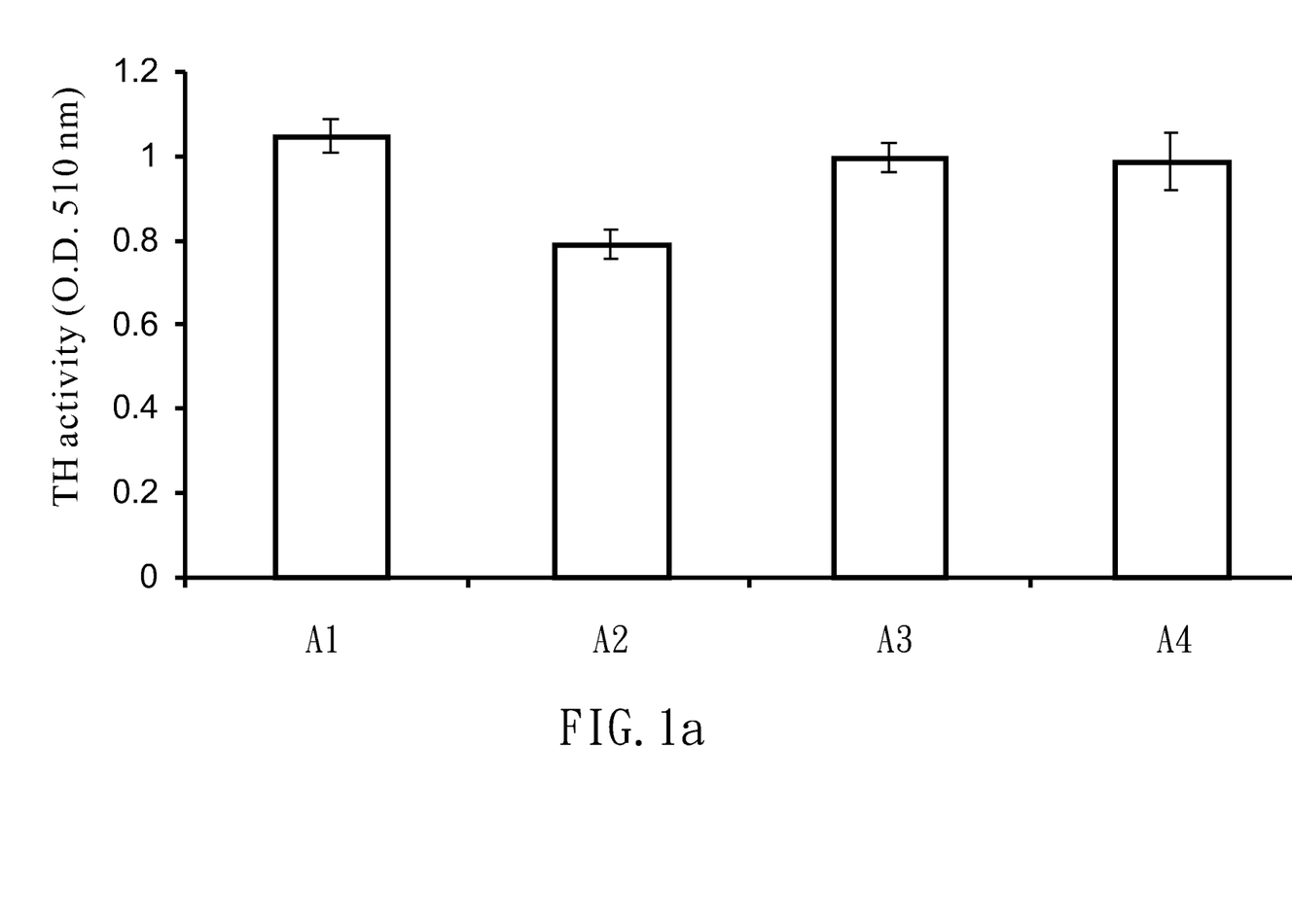
FIG. 1a depicts tyrosine hydroxylase activity of white shrimps of groups A1-A4 in trial (A).

Referring to FIG. 1a, tyrosine hydroxylase activity in white shrimps of group A2 is significantly lower than that of white shrimps of groups A1 and A3-A4.

Moreover, tyrosine hydroxylase is known as an important enzyme to form dopamine and epinephrine, and overexpression of both dopamine and epinephrine may reduce immunity of white shrimps.

Figure 1B:
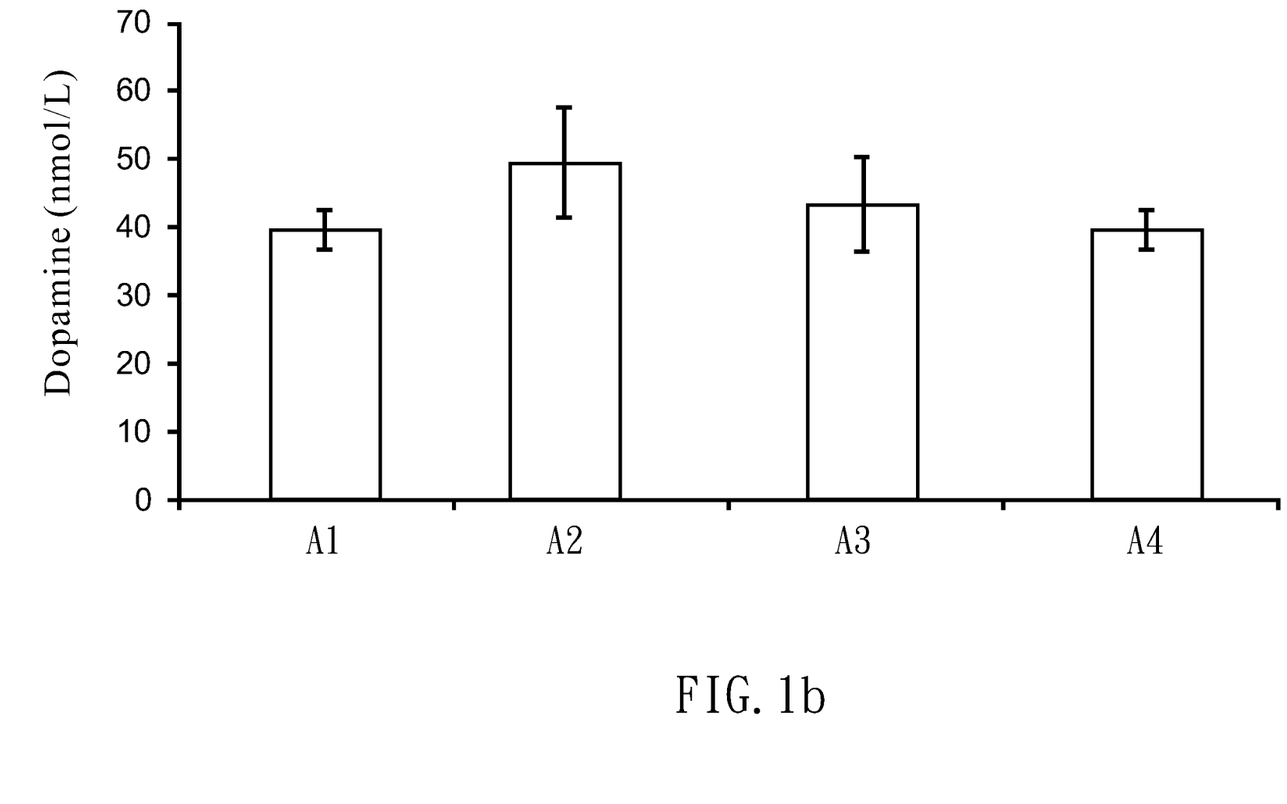
FIG. 1b depicts dopamine level of White shrimps of groups A1-A4 in trial (A).
Figure 1C:
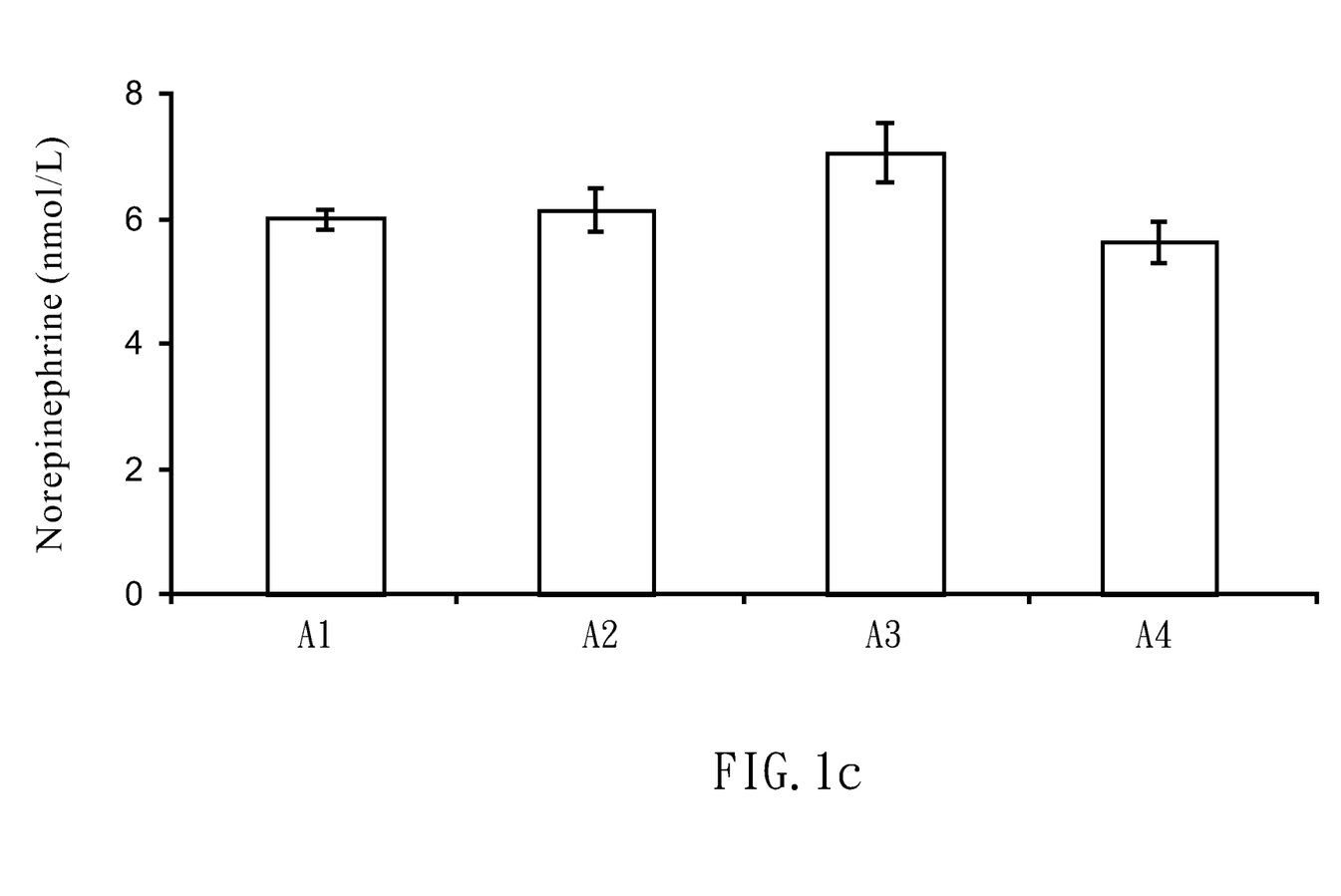
FIG. 1c depicts norepinephrine level of white shrimps of groups A1-A4 in trial (A).

Therefore, to demonstrate whether the TH dsRNA improves immunity by inhibiting both dopamine and epinephrine, dopamine level and epinephrine level of white shrimps of groups A1-A4 are measured. Referred to FIGS. 1b and 1c, no significant difference in dopamine and epinephrine levels is observed among white shrimps of groups A1-A4.

Trial (B)

The dsRNA shown in TABLE 2 is administered to white shrimps of groups B2-B4 (dosage: 5 μg/g). After 3 days, hymolymph is withdrawn from the ventral sinus of each shrimp. Immune parameters, such as total haemocyte count (THC) and phenoloxidase (PO) activity in the haemocytes, of white shrimps of groups B1-B4 are measured.

TABLE 2

| Group | double-stranded RNA |
|---|---|
| B1 | DEPC-H$_2$O |
| B2 | dsRNA specific to tyrosine hydroxylase (SEQ ID NOS: 1 and 2) |
| B3 | dsRNA specific to glyceraldehydes 3-phosphate dehydrogenase (SEQ ID NOS: 7 and 8) |
| B4 | dsRNA specific to worm non-specific gene (SEQ ID NOS: 9 and 10) |

Figure 2A:
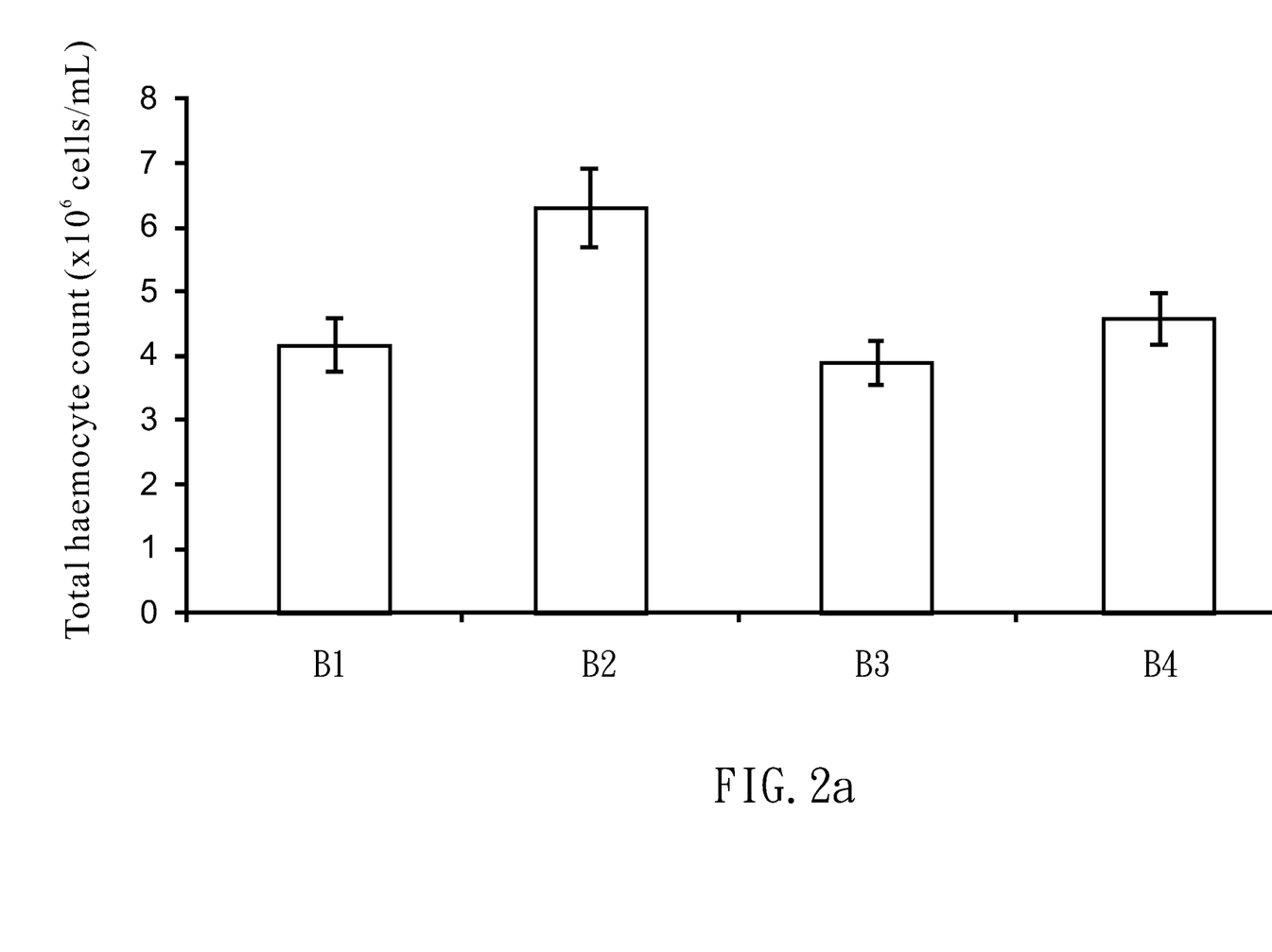
FIG. 2a depicts total haemocyte count of white shrimps of groups B1-B4 in trial (B).
Figure 2B:
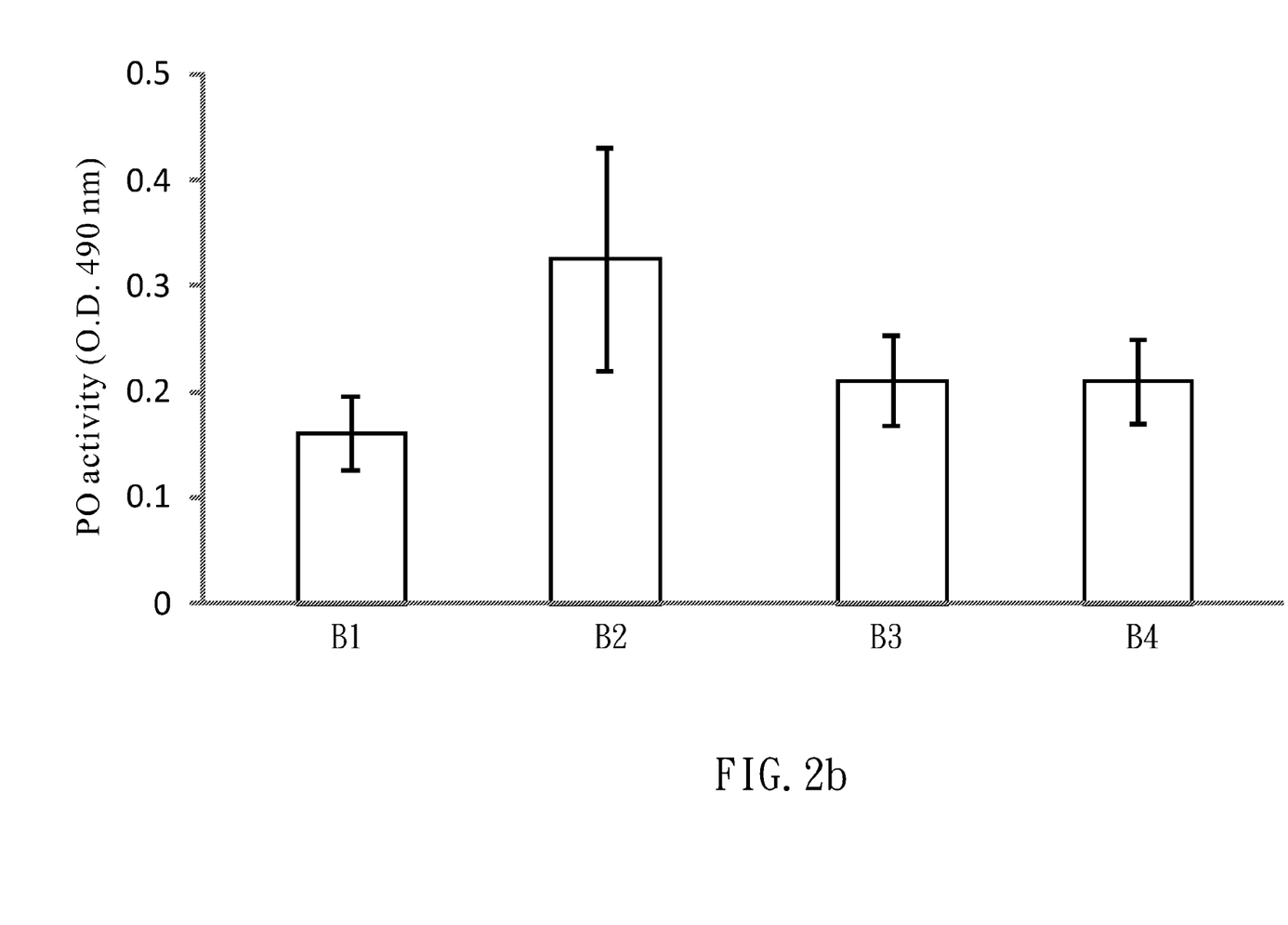
FIG. 2b depicts phenoloxidase activity of white shrimps of groups B1-B4 in trial (B).

Referring to FIGS. 2a and 2b, immune parameters of white shrimps of group B2 are higher compared to those of white shrimps of groups B1 and B3-B4, indicating the administration of the TH dsRNA improves immunity of white shrimps.

Trial (C)

The dsRNA shown in TABLE 3 is administered to white shrimps of groups C2-C4 (dosage: 5 μg/g). After 3 days, V. alginolyticus bacterial suspension is used to challenge white shrimps of groups C1-C4 (dosage: 2*10$^5$ CFU/shrimp) for 1.5 hours. Hymolymph is withdrawn from the ventral sinus of each shrimp. For the susceptibility of white shrimps received TH dsRNA against V. alhinolyticus infection, phagocytic activity and clearance efficiency of white shrimps of groups C1-C4 are measured.

TABLE 3

| Group | double-stranded RNA |
|---|---|
| C1 | DEPC-H$_2$O |
| C2 | dsRNA specific to tyrosine hydroxylase (SEQ ID NOS: 1 and 2) |
| C3 | dsRNA specific to glyceraldehydes 3-phosphate dehydrogenase (SEQ ID NOS: 7 and 8) |
| C4 | dsRNA specific to worm non-specific gene (SEQ ID NOS: 9 and 10) |

Figure 3A:
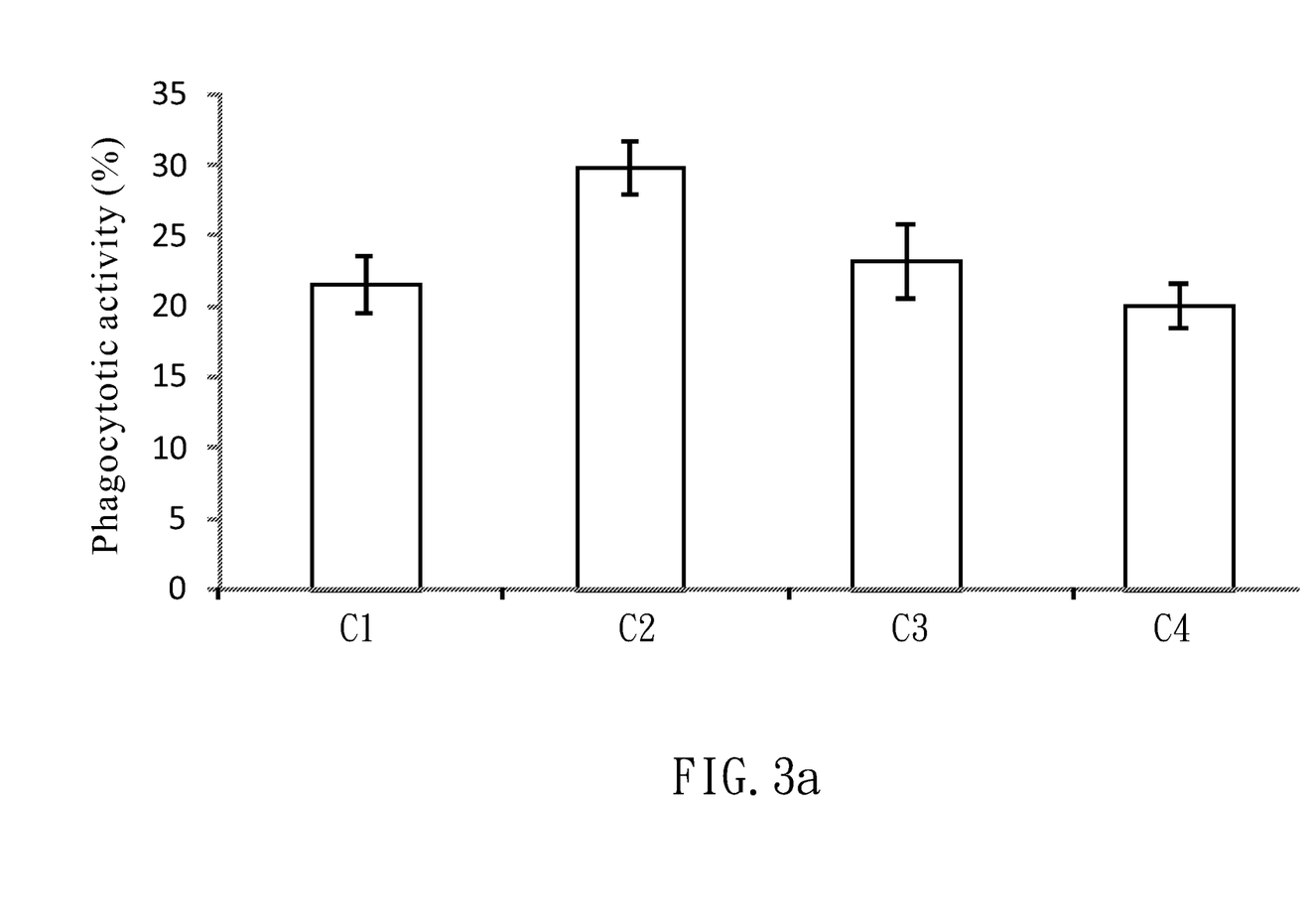
FIG. 3a depicts phagocytic activity of white shrimps of groups C1-C4 in trial (C).
Figure 3B:
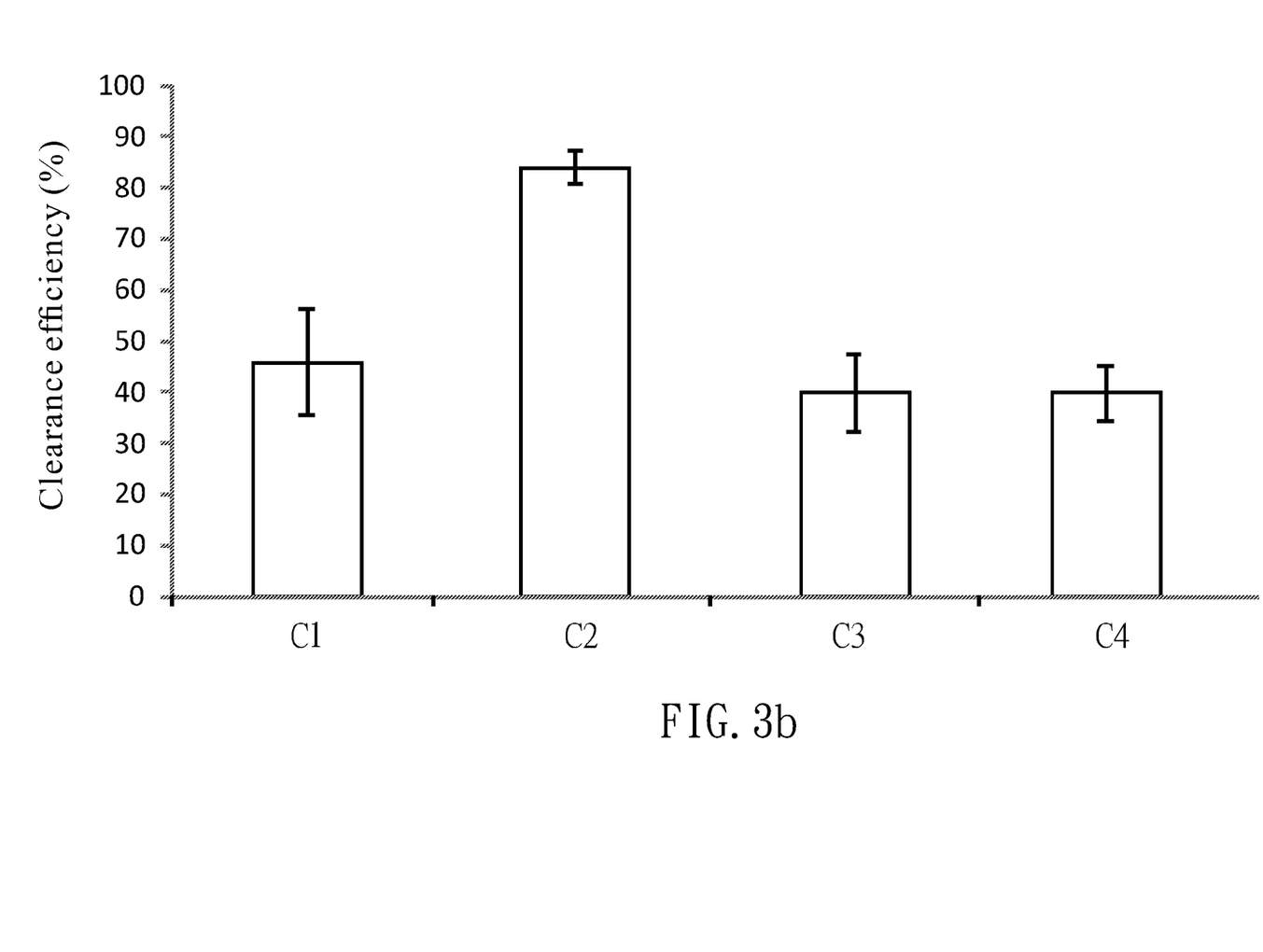
FIG. 3b depicts clearance efficiency of white shrimps of groups C1-C4 in trial (C).

Referring to FIGS. 3a and 3b, phagocytic activity and clearance efficiency are significantly higher in white shrimps of group C2 than in white shrimps of groups C1 and C3-C4, indicating the administration of the TH dsRNA is helpful to deplete V. alginolyticus in hymolymph.

Trial (D) V. alginolyticus Challenging Test

For the susceptibility of white shrimps received TH dsRNA against V. alhinolyticus infection, the dsRNAs shown in TABLE 4 are administered to white shrimps of groups D2-D4 (dosage: 5 μg/g). After 3 days, V. alginolyticus bacterial suspension is used to challenge white shrimps of groups D1-D4 (dosage: 2*10$^5$ CFU/shrimp). The mortality is recoded at 0, 6, 12, 24, 48, 72, 96, 120, 144 and 168 hours.

TABLE 4

| Group | V. alginolyticus | double-stranded RNA |
|---|---|---|
| D0 | − | DEPC-H$_2$O |
| D1 | + | DEPC-H$_2$O |
| D2 | + | dsRNA specific to tyrosine hydroxylase (SEQ ID NOS: 1 and 2) |
| D3 | + | dsRNA specific to glyceraldehydes 3-phosphate dehydrogenase (SEQ ID NOS: 7 and 8) |
| D4 | + | dsRNA specific to worm non-specific gene (SEQ ID NOS: 9 and 10) |

Figure 4:
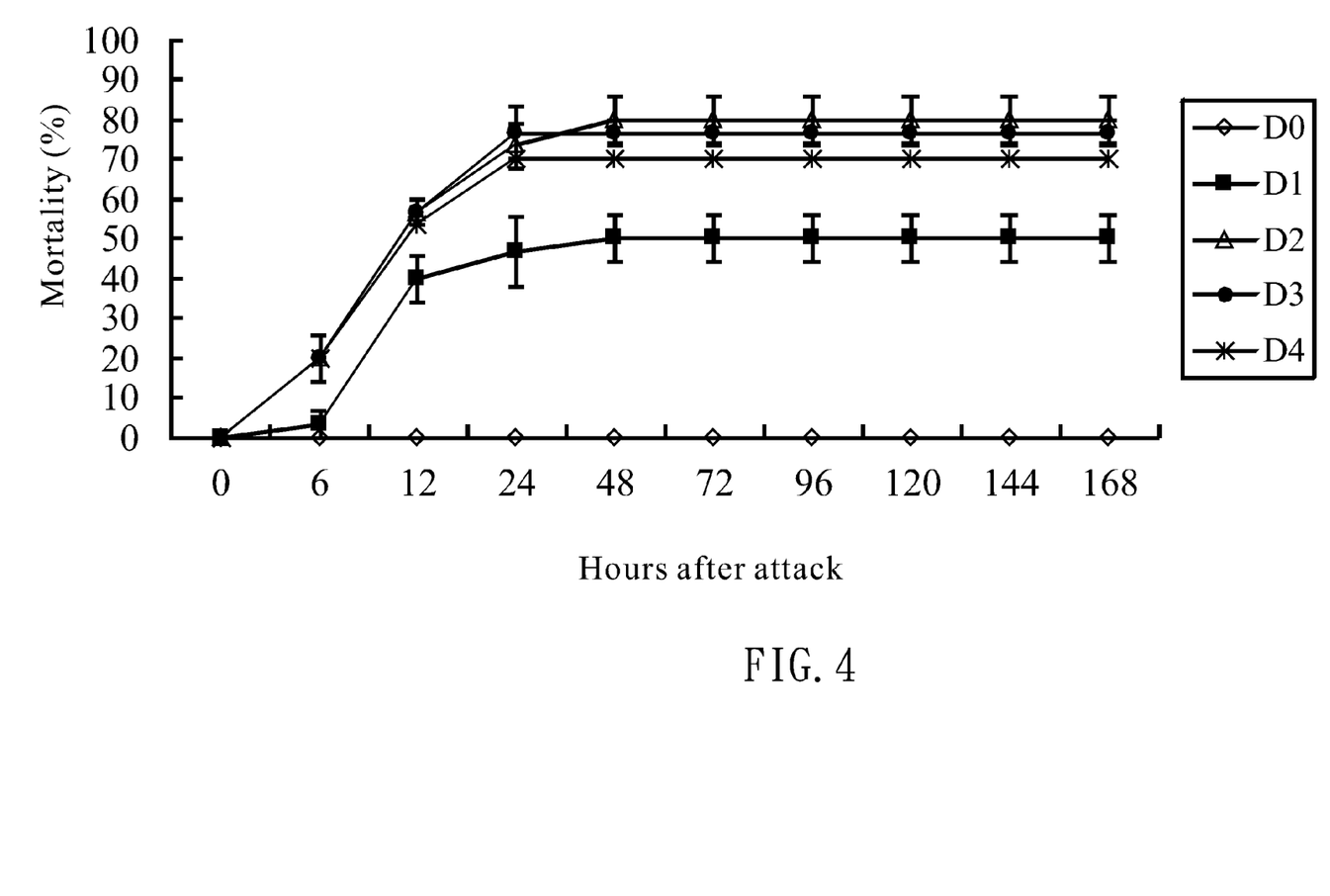
FIG. 4 depicts mortality of white shrimps of groups D0-D4 in trial (D).

Referring to FIG. 4, at 168 hours post bacterial challenge, the cumulative mortality of white shrimps of group D0 is 0, and the cumulative mortality of white shrimps of groups D1, D3-D4 is about 70-80%. However, the cumulative mortality of white shrimps of group D2 decreases (about 50%), indicating the administration of the TH dsRNA effectively reduces the risk of death due to infection of V. alginolyticus in white shrimps.

Accordingly, by administering the double-stranded RNA specific to tyrosine hydroxylase (TH dsRNA) to the shrimp body, immune parameters such as total haemocyte count and phenoloxidase activity are improved, phagocytic activity and clearance efficiency are increased, and mortality caused by attack of pathogens is decreased. With such performance, farmers can decrease the usage of antibiotics.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for improving immunity in shrimps, by administering a double-stranded RNA specific to tyrosine hydroxylase to a shrimp body to improve immunity of the shrimp body.

2. The method for improving immunity in shrimps as claimed in claim 1, wherein the double-stranded RNA has a DNA sequences set forth as SEQ ID NOS: 1 and 2.

3. The method for improving immunity in shrimps as claimed in claim 1, wherein the double-stranded RNA has a DNA sequences set forth as SEQ ID NOS: 3 and 4.

4. The method for improving immunity in shrimps as claimed in claim 1, wherein the double-stranded RNA has a DNA sequences set forth as SEQ ID NOS: 5 and 6.

5. The method for improving immunity in shrimps as claimed in claim 1, wherein the double-stranded RNA is administered to the shrimp body by injection.

6. The method for improving immunity in shrimps as claimed in claim 5, wherein the double-stranded RNA is administered to the shrimp body by injection into the ventral sinus of the cephalothorax.

7. The method for improving immunity in shrimps as claimed in claim 1, wherein the shrimp body is $11.63 \pm 2.1$ g.

8. The method for improving immunity in shrimps as claimed in claim 1, wherein the double-stranded RNA is administered to the shrimp body in a dosage of 1-6 µg/g of the shrimp body.

9. The method for improving immunity in shrimps as claimed in claim 8, wherein the double-stranded RNA is administered to the shrimp body in a dosage of 5 µg/g of the shrimp body.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: LvTH dsRNA

<400> SEQUENCE: 1
gcaucacucu ucgaucaaat t                                              21

<210> SEQ ID NO 2
<211> LENGTH: 21
<212> TYPE: DNA
<213> ORGANISM: Artificial Sequence
<220> FEATURE:
<223> OTHER INFORMATION: LvTH dsRNA

<400> SEQUENCE: 2
uuugaucgaa gagugaugct t                                              21

<210> SEQ ID NO 3
<211> LENGTH: 21
<212> TYPE: DNA
<213> ORGANISM: Artificial Sequence
<220> FEATURE:
<223> OTHER INFORMATION: LvTH dsRNA

<400> SEQUENCE: 3
ccaaguucga gagcaccaut t                                              21

<210> SEQ ID NO 4
<211> LENGTH: 21
<212> TYPE: DNA
<213> ORGANISM: Artificial Sequence
<220> FEATURE:
<223> OTHER INFORMATION: LvTH dsRNA

<400> SEQUENCE: 4
auggugcucu cgaacuuggt t                                              21

<210> SEQ ID NO 5
<211> LENGTH: 21
<212> TYPE: DNA
<213> ORGANISM: Artificial Sequence
<220> FEATURE:
<223> OTHER INFORMATION: LvTH dsRNA

<400> SEQUENCE: 5
ccaggagauc gagaaguuut t                                              21

<210> SEQ ID NO 6
<211> LENGTH: 21
<212> TYPE: DNA
<213> ORGANISM: Artificial Sequence
<220> FEATURE:
<223> OTHER INFORMATION: LvTH dsRNA

<400> SEQUENCE: 6
aaacuucucg aucuccuggt t                                              21

<210> SEQ ID NO 7
<211> LENGTH: 21
<212> TYPE: DNA
<213> ORGANISM: Artificial Sequence

```
<220> FEATURE:
<223> OTHER INFORMATION: GAPDH dsRNA

<400> SEQUENCE: 7
ugaccucaac uacaugguut t                                              21

<210> SEQ ID NO 8
<211> LENGTH: 21
<212> TYPE: DNA
<213> ORGANISM: Artificial Sequence
<220> FEATURE:
<223> OTHER INFORMATION: GAPDH dsRNA

<400> SEQUENCE: 8
aaccauguag uugaggucat t                                              21

<210> SEQ ID NO 9
<211> LENGTH: 21
<212> TYPE: DNA
<213> ORGANISM: Artificial Sequence
<220> FEATURE:
<223> OTHER INFORMATION: worm dsRNA

<400> SEQUENCE: 9
uucuccgaac gugucacgut t                                              21

<210> SEQ ID NO 10
<211> LENGTH: 21
<212> TYPE: DNA
<213> ORGANISM: Artificial Sequence
<220> FEATURE:
<223> OTHER INFORMATION: worm dsRNA

<400> SEQUENCE: 10
acgugacacg uucggagaat t                                              21
```